United States Patent [19]

Yano et al.

[11] Patent Number: 5,532,323
[45] Date of Patent: Jul. 2, 1996

[54] METHOD FOR PRODUCTION OF ABSORBENT RESIN

[75] Inventors: Kazutaka Yano; Katsuhiro Kajikawa; Kinya Nagasuna; Yoshio Irie, all of Himeji, Japan

[73] Assignee: Nippon Shokubai Co., Ltd., Osaka, Japan

[21] Appl. No.: 26,407

[22] Filed: Mar. 4, 1993

[30] Foreign Application Priority Data

Mar. 5, 1992 [JP] Japan .................................. 4-048321

[51] Int. Cl.$^6$ .................................. C08F 8/14; C08J 3/24
[52] U.S. Cl. .................. 525/384; 526/240; 526/318.41; 526/320; 526/73; 528/481
[58] Field of Search ............... 526/240, 318.41, 526/320, 73; 525/384; 528/481

[56] References Cited

U.S. PATENT DOCUMENTS

| | | | |
|---|---|---|---|
| 3,976,614 | 8/1976 | Elms et al. ........................ | 526/320 X |
| 4,351,922 | 9/1982 | Yoshida et al. ..................... | 525/116 |
| 4,812,486 | 3/1989 | Hosokawa et al. ................... | 521/139 |
| 4,863,989 | 9/1989 | Obayashi et al. .................... | 524/419 |
| 4,873,299 | 10/1989 | Nowakowsky et al. ............... | 526/73 |
| 4,959,060 | 9/1990 | Shimomura et al. ................. | 604/368 |
| 4,962,172 | 10/1990 | Allen et al. ........................ | 526/318.42 |
| 4,972,019 | 11/1990 | Obayashi et al. .................... | 524/83 |
| 5,073,612 | 12/1991 | Irie et al. ........................... | 526/240 |
| 5,280,078 | 1/1994 | Gregor et al. ...................... | 525/328.5 |
| 5,281,683 | 1/1994 | Yano et al. ........................ | 526/323.2 |

OTHER PUBLICATIONS

Hawley's Condensed Chemical Dictionary, 11th Ed (NISax et al, eds.) pp. 53, 64–72, Van Nostrand Reinhold, New York, 1987.
R N Morrison and R N Boyd Organic Chemistry 3rd Ed Allyn and Bacon, Boston (1973) pp. 729, 731.

*Primary Examiner*—Mark Nagumo
*Attorney, Agent, or Firm*—Burns, Doane, Swecker & Mathis

[57] ABSTRACT

An absorbent resin exhibiting a high absorption ratio, having only a small water-soluble component content, and have excellent gel stability to withstand the effect of aging is produced. The production of the absorbent resin comprises a step of polymerizing a water-soluble monoethylenically unsaturated monomer by using, in a proportion of 0.01–0.3 mol % based on the amount of the water-soluble monoethylenically unsaturated monomer, a cross-linking agent having at least one group of the following formula I:

$$-(-CH_2CH_2OR^1O-)- \qquad (I)$$

wherein $R^1$ is an alkylene group of 2 to 4 carbon atoms interposed between two polymerizing unsaturated groups in the molecular unit thereof and then heat-treating the resin produced by the polymerization at a temperature in the range of from 160° to 230° C.

6 Claims, No Drawings

METHOD FOR PRODUCTION OF ABSORBENT RESIN

BACKGROUND OF THE INVENTION

1. Field of the Invention

This invention relates to a method for the production of an absorbent resin. More particularly, it relates to a method for the production of an absorbent resin having a high absorption ratio, having a small water-soluble component, and having excellent in stability to resist the effect of aging.

2. Description of the Prior Art

The absorbent resins have heretofore found utility in various absorbent materials such as paper diapers (or disposable diapers), sanitary articles, and water-retaining agents for soil. The absorbent resins of this type which have been known to the art include hydrolyzed starch-acrylonitrile graft copolymer, neutralized starch-acrylic acid graft copolymer, cross-linked acrylic acid or acrylate polymer, partially cross-linked polyethylene oxide, and cross-linked carboxymethyl cellulose, for example.

In the cross-linked polymers mentioned above, those cross-linked polymers which are obtained by copolymerizing acrylic acid and other water-soluble monoethylenically unsaturated monomers in the presence of a cross-linking monomer form the mainstream of absorbent resins because they use inexpensive raw materials, excel in absorption characteristics, and have no possibility of putrefaction (JP-A-60-24807 and U.S. Pat. No. 4,351,922).

These absorbent resins, however, are generally such that the content of water-soluble components (which are soluble in water) increases proportionally as their absorption ratios rise. When an absorbent resin having a high water-soluble component content is used for a long time as in a diaper, for example, it has the problem of forming a ropy surface on the diaper or the problem of rendering the diaper leaky because the absorbent impairs the perviousness of the diaper to liquid so much that it degrades the practical absorbency of the diaper and the diffusibility of liquid in the diaper. When the amount of a cross-linking agent to be used in the absorbent resin is increased for the purpose of proportionally decreasing the content of water-soluble components therein, the absorption ratio of the absorbent resin is lowered and the range of uses found for the absorbent resin is limited.

In addition to the problem of the content of water-soluble components mentioned above, the absorbent resins have the problem of poor stability arising from the ability of a swelled gel of resin to withstand the effect of aging. When an absorbent resin is used as in a diaper, for example, the swelled gel which the absorbent resin produces on absorbing urine deteriorates (fluidization of the gel) with the elapse of time and eventually leads to a reduction of the absorption characteristics. Likewise, when an absorbent resin is used for a long time in agronomic operations, there is the possibility of it undergoing degradation and decomposition.

As a means for preventing the swelled gel of absorbent resin from undergoing degradation and decomposition, methods which rely on the incorporation of an oxygen-containing reducing inorganic salt or a radical chain inhibitor in the absorbent resin (JP-A 63-118375 and JP-A 63-152667), a method which cause an oxidizing agent to be contained in the absorbent resin (JP-A 63-153060), and a method which causes a sulfur-containing reducing agent to be contained in the absorbent resin (JP-A 63-272349) have been known to the art. However, these methods, invariably necessitate the use of additives in the absorbent resin for the sake of limiting deterioration of the absorbent resin. The use of such additives in the absorbent resin is not always desirable in terms of safety in the light of the fact that the absorbent resin may possibly be used in sanitary articles.

Another method has been proposed which enables the absorbent resin to acquire improved stability to withstand the effect of aging by using the cross-linking agent in an increased amount thereby heightening the cross-linking density of the absorbent resin and enhancing the gel strength. Imparting sufficient stability to the absorbent resin to resist the effect of aging has the disadvantage of extremely lowering the absorption ratio of the absorbent resin because of the high degree of cross-linking.

An object of this invention, therefore, is to provide a novel method for the production of an absorbent resin.

Another object of this invention is to provide a method for the production of an absorbent resin which has a high absorption ratio, contains a water-soluble component only in a small proportion, and excels in stability to withstand the effect of aging.

SUMMARY OF THE INVENTION

These objects are accomplished by a method for producing an absorbent resin by polymerizing a water-soluble monoethylenically unsaturated monomer in the presence of a cross-linking agent and heat-treating the resultant polymer, which method of production is characterized by the fact that the cross-linking agent is a cross-linking agent possessing at least two polymerizable unsaturated groups and further possessing between the two polymerizable unsaturated groups at least one unit represented by the formula I:

$$\text{--}(CH_2CH_2OR^1O\text{)--} \qquad (I)$$

wherein $R^1$ is an alkylene group of 2 to 4 carbon atoms, this cross-linking agent is used in a proportion in the range of from 0.01 to 0.3 mol % based on the amount of the water-soluble monoethylenically unsaturated monomer, and the heat treatment is carried out at a temperature in the range of from 160° to 230° C.

The absorbent resin which is obtained by the method of this invention has a high absorption ratio, contains a small proportion of water-soluble component and has excellent stability to withstand the effects of aging as compared with the conventional absorbent resins and, therefore, only sparingly produces a sensation of ropiness when swelled, exhibits satisfactory perviousness to liquid, and retains these desirable properties for a long time. Thus, it finds extensive utility in sanitary articles, civil engineering materials, agronomic tools, etc.

DESCRIPTION OF THE PREFERRED EMBODIMENTS

The water-soluble monoethylenically unsaturated monomer to be used in this invention has no particular restriction except for the requirement that it should be a monomer which possesses one ethylenically unsaturated group and exhibits solubility in water. The water-soluble monoethylenically unsaturated monomers which are effectively usable herein include acid group-containing monomers such as (meth)acrylic acid, itaconic acid, 2-(meth)acryloyl ethanesulfonic acid, 2-(meth)acryloyl propanesulfonic acid, 2-(meth)acrylamide-2-methylpropanesulfonic acid, vinyl sulfonic acid, and styrene sulfonic acid; metal salts, ammonium salts, and amine salts of the acid radical-containing monomers mentioned above; nonionic hydrophilic group-containing monomers such as (meth)acrylamides and alkoxypolyethylene glycol (meth)acrylates; amino group-containing monomers such as diethyl aminoethyl-(meth)acrylate, diethyl aminopropyl(meth)acrylate, and dimethyl aminopropyl(meth)acrylamide; and quaternization products of an amino group-containing monomer mentioned above, for example. One member or a mixture of two or more members selected from the group of water-soluble monoethylenically unsaturated monomers enumerated above may be used.

Preferably, the water-soluble monoethylenically unsaturated monomer is a monomer which contains 50% by weight or more of at least one member selected from the group consisting of acrylic acid and alkali metal salts, ammonium salt, and amine salt thereof. The salts mentioned above preferably have a neutralization ratio in the range of from 30 to 80%. The neutralization may be effected after the polymerization.

The water-soluble monoethylenically unsaturated monomer may be used in combination with other monomers added thereto in an amount not large enough as to seriously impair the quality of the absorbent resin to be produced. Further, the water-soluble monoethylenically unsaturated monomer may incorporate therein a natural macromolecular substance such as starch, cellulose, or polyvinyl alcohol or a synthetic polymeric substance as a grafting component when it is subjected to polymerization. The other monomers which are effectively usable herein in combination with the water-soluble monoethylenically unsaturated monomer include methyl (meth)acrylates, ethyl (meth)acrylates, butyl (meth)acrylate, vinyl acetate, and vinyl propionate, for example. Optionally, a mixture of two or more of these monomers may be used.

The cross-linking agent (hereinafter referred to cross-linking agent (I)) to be used in this invention is a compound which has at least one unit represented by the following formula I:

$$+CH_2CH_2OR^1O+ \quad (I)$$

wherein $R^1$ is an alkylene group of 2 to 4 carbon atoms, interposed between at least two polymerizable unsaturated groups. The alkylene group of 2 to 4 carbon atoms may be either in the linear structure or in the branched structure. The following groups are typical examples.

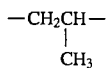
$$-CH_2CH- \\ \phantom{-CH_2}|\phantom{CH} \\ \phantom{-CH_2}CH_3 \quad (II)$$

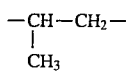
$$-CH-CH_2- \\ \phantom{-}|\phantom{-CH_2CH_2} \\ \phantom{-}CH_3 \quad (III)$$

$$-CH_2CH_2CH_2CH_2- \quad (IV)$$

The molecular weight of the cross-linking agent (I) preferably does not exceed 6,000. Preferably, it is in the range of from 214 to 5,000, most preferably in the range of 214 to 2,500.

Typical examples of the cross-linking agent are compounds of the structure represented by the following formula V:

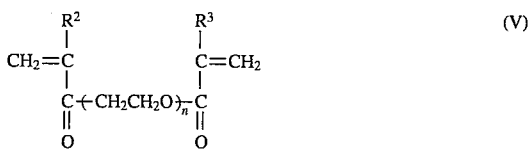

wherein $R^2$ and $R^3$ are independently a hydrogen atom or a methyl group and n is a numeral of from 2 to 100, preferably from 2 to 50, and compounds of the structure represented by the following formula VI:

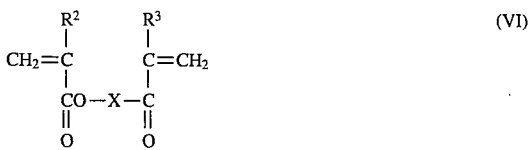

wherein $R^2$ and $R^3$ are independently a hydrogen atom or a methyl group and X is a divalent organic group having 1 to 100, preferably 1 to 50, and structural units (A) represented by the formula, —$CH_2CH_2O$—, and 1 to 20, preferably 1 to 10, structural units (B) represented by the formula, —$R^4O$—, wherein $R^4$ is an alkylene group of 3 or 4 carbon atoms, linearly joined in an arbitrary order or a divalent organic group having 1 to 5, preferably 1 to 3, structural units (C) represented by the formula, —(CO—CH=CH—CO—O)—, 2 to 100, preferably 4 to 50, structural units (D) represented by the formula —$CH_2CH_2O$— and 0 to 20, preferably 0 to 10, structural units (E) represented by the formula —$R^5O$—, wherein $R^5$ is an alkylene group having 3 to 4 carbon atoms linearly joined in an arbitrary order.

The alkylene group of 3 or 4 carbon atoms may be either in the linear structure or in the branched structure similar to $R^1$ mentioned above.

As the typical cross-linking agent (I), there are, for example, polyethylene glycol di(meth)-acrylate, di(meth)acrylate of a polyethylene glycol-polypropylene glycol block copolymer, di(meth)acrylate of a polyethylene glycol-polypropylene glycol random copolymer, fumaric acid di[polyethylene glycol mono(meth)acrylate] esters, maleic acid di[polyethylene glycol mono(meth)acrylate] esters, etc.

In this invention, any of the cross-linking agents well known heretofore in the art may be used as a second cross-linking agent (hereinafter referred to cross-linking agent (II)) in a small amount in combination with the cross-linking agent possessing the unit represented by the formula I. The amount of the second cross-linking agent to be optionally used generally is not more than 0.01 mol % based on the amount of the water-soluble ethylenically unsaturated monomer.

It is essential that the cross-linking agent (I) should be used in a proportion in the range of from 0.01 to 0.3 mol % based on the amount of the water-soluble monoethylenically unsaturated monomer, in due consideration of the objects of this invention. If the amount of the cross-linking agent is less than 0.01 mol %, the possibility arises that the content of water-soluble component will unduly increase in the absorbent resin to be produced. Conversely, if this amount exceeds 0.3 mol %, the possibility ensues that the heat treatment will produce no significant improvement in the absorption characteristics of the produced absorbent resin. Preferably, this amount is in the range of from 0.03 to 0.2 mol %.

In this invention, virtually any method may be adopted for effecting the polymerization of a water-soluble monoethylenically unsaturated monomer in the presence of the cross-linking agent (I) mentioned above. Preferably, the method which comprises polymerizing an aqueous solution of monomer components including a water-soluble monoethylenically unsaturated monomer in the presence of the cross-linking agent (I) mentioned above is used. As the method of polymerization, various methods such as aqueous solution polymerization, reversed-phase suspension polymerization are available. Particularly, the aqueous solution polymerization method or the reverse-phase suspension polymerization method prove favorable in consideration of the workability during the polymerization and the absorption characteristics of the absorbent resin to be produced.

For initiating the polymerization, any of various known methods such as, for example, the method which relies on use of a radical polymerization initiator and the method which resorts to irradiation with radiation, electron beam, or ultraviolet light (in the case of the irradiation of ultraviolet light, a photopolymerization initiator may be additionally used) can be adopted. The radical polymerization initiators which may be used effectively herein include water-soluble radical polymerization initiators in popular use which are represented by persulfates such as potassium persulfate, sodium persulfate, and ammonium persulfate; hydroperoxides such as hydrogen peroxide, t-butyl hydroperoxide, and cumene hydroperoxide; and azo compounds such as 2,2-azobis-2-amidinopropane hydrochloride, for example. One member or a mixture of two or more members selected from the group of radical polymerization initiators mentioned above may be used. It is also permissible to use a redox initiator which is produced by combining such a radical polymerization initiator with a reducing agent such as, for example, a sulfite, ferrous compound, and L-ascorbic acid. The amount of the radical polymerization initiator to be used is preferably in the range of from 0.01 to 1.0% by weight, most preferably from 0.005 to 0.5% by weight, based on the amount of the monomer.

When the polymer is synthesized by the aqueous solution polymerization method or the reversed-phase suspension polymerization method, the monomer is generally used in the form of an aqueous solution. Though the monomer concentration in the aqueous monomer solution can be selected in a wide range, it is generally preferable to be at least 20% by weight, more preferably to be between 25% by weight as the minimum and the saturated concentration. The synthesis may be performed, when necessary, in the presence of an organic solvent. The organic solvents which are effectively usable herein include alcohols compatible with water such as methanol, ethanol, propanol, and butanol; ethers compatible with water such as tetrahydrofuran and dioxane; ketones compatible with water such as acetone and methylethyl ketone; nitriles compatible with water such as acetonitrile; and amide compatible with water such as N,N-dibutyl formamide, for example.

The temperature of the polymerization, though widely variable depending on the kind of the radical polymerization initiator used, generally is in the range of from 0° to 150° C., preferably from 10° to 100° C. The pressure of the atmosphere which envelopes the site of polymerization may be suitably set at a level between a vacuum and an increased pressure.

The polymerization temperature may be controlled by selecting the combination of the kind and amount of the radical polymerization initiator to be used and the ambient pressure.

For this invention, it is essential that the polymer obtained by the polymerization should be heat-treated in a specific temperature range of from 160° to 230° C. If the heat treatment is performed at a temperature below 160° C. or above 230° C., the absorbent resin to be obtained suffers from an unduly low absorption ratio and an unduly large content of water-soluble component for the absorption ratio. Preferably, the temperature of the heat treatment is in the range of from 180° to 200° C. In preparation for the heat treatment, the polymer is preferable to be in a hydrated state. The water content of the polymer prior to the heat treatment is desired to be in the range of from 30 to 95% by weight, preferably from 60 to 95% by weight.

As concrete ways of heat-treating the polymer in the hydrated state in the specific temperature range mentioned above, a method which comprises drying the polymer in the hydrated state simultaneously with the heat treatment, a method which performs the heat treatment after the polymer has been adjusted to the optimum water content by addition of water, a method which comprises heating the polymer in the hydrated state at a temperature not exceeding 160° C. thereby decreasing the water content of the polymer and subsequently subjecting the resultant resin to the heat treatment, and a method which comprises subjecting the polymer in the hydrated state without a notable loss of the water content to the heat treatment may be cited, for example.

The absorbent resin which is obtained in consequence of the heat treatment, when necessary, may be dried and, when further necessary, may be pulverized, classified, and finished as a product.

For the heat treatment of this invention, any of the conventional drying devices and heating furnaces may be used. The devices which are effectively usable for the heat treatment include a grooved agitating drier, a rotary drier, a disc drier, a kneading drier, a hot air drier, a fluidized bed drier, an air current drier, an infrared drier, and an induction heating drier, for example.

For the purpose of accomplishing the objects of this invention, it is advantageous to perform the polymerization under conditions so selected that the absorption ratio of the absorbent resin obtained by the heat treatment at a temperature deviating from the specific temperature range of this invention is less than 55 g/g, more desirably less than 50 g/g, whereas the absorption ratio of the absorbent resin obtained by the heat treatment at a temperature in the specific temperature range of this invention is 55 g/g or more. When the resin obtained by heat-treating the polymer at a temperature deviating from the specific temperature range of this invention assumes an absorption ratio of 55 g/g or more, the heat treatment similarly performed at a temperature in the specific temperature range of this invention tends to give an increased water-soluble component content to the produced resin. As a result, the possibility may arise that the absorbent resin having a high absorption ratio and a low content of water-soluble component as required at by this invention will not be obtained. For the purpose of lowering below 55 g/g the absorption ratio of the resin obtained by the heat treatment at a temperature deviating from the specific temperature range of this invention, it is sufficient to suitably adjust the type and/or amount of the cross-linking agent (I) to be used in the production of the polymer or to use the cross-linking monomer (I) in combination with the second cross-linking agent.

In preparation for the heat treatment of the polymer at a temperature in the specific temperature range of this invention, the polymer may be mixed with a third cross-linking agent (hereinafter referred to cross-linking agent (III)) which has two or more functional groups capable of reacting with the functional group of the polymer. Therefore, when the heat treatment starts, the polymer reacts with the cross-linking agent (III) in the surface part of the reaction system so as to enhance the cross-linking density in the surface region of the polymer particles and further improve the produced absorbent resin in the absorption characteristics and the stability to withstand the effect of aging.

The compounds which are effectively usable herein as the cross-linking agent (III) on the condition that the absorbent resin possesses a carboxyl group include polyalcohols, polyglycidyl ethers, polyamines, polyaziridines, polyisocyanates, alkylene carbonates, and polyvalent metal salts, for example. The amount of the cross-linking agent (III) preferably used herein is in the range of from 0.005 to 5 parts by weight, most preferably from 0.01 to 1 parts by weight, based on the amount of solids taken as 100 parts by weight. When the cross-linking agent (III) is mixed with the polymer before the heat treatment or with the absorbent resin after the heat treatment, it is beneficial to use water or a hydrophilic organic solvent for the purpose of controlling the infiltration of the cross-linking (III) into the polymer. The hydrophilic organic solvents which are effectively usable herein include alcohols such as methanol, ethanol, and propanol; ethers such as tetrahydrofuran and dioxane; ketones such as acetone and methylethyl ketone; and nitriles such as acetonitrile, for example. These hydrophilic organic solvents may be used either singly or in the form of a mixture of two or more members. The cross-linking treatment by the use of this cross-linking agent (III) may be performed on the absorbent resin which is obtained in consequence of the heat treatment.

Now, this invention will be described more specifically below with reference to working examples and comparative experiments. This invention is not limited to the working examples. The absorption ratio, the water-soluble component content, the ropiness of the gel, and the stability of the gel to withstand the effect of aging which were obtained from the absorbent resins produced in the working examples and comparative experiments were determined as follows.

(a) Absorption ratio

About 0.200 g of a given absorbent resin powder was sampled, weighed accurately, and uniformly placed in a tea bag type pouch (40 mm×50 mm) made of non-woven fabric. The pouch containing the sample was immersed in an aqueous 0.9% sodium chloride solution and left standing therein for 30 minutes. At the end of that time, the wet pouch was weighed. The same tea bag type pouch empty of a sample was similarly impregnated with the aqueous solution. The wet pouch was used as a blank. The absorption ratio of the sample absorbent resin was calculated in accordance with the following formula 1:

Absorption ratio (g/g)=[weight after absorption (g)−Blank (g)]/ [accurate weight of absorbent resin powder (g)]tm (1)

(b) Content of water-soluble component

About 0.500 g of a given absorbent resin powder was dispersed in 1,000 ml of deionized water and stirred therein for 12 hours. The resultant suspension was filtered through a filter paper. The filtrate was analysed for the solids content. The content of water-soluble component of the sample was determined in accordance with the following formula 2:

Content of water-soluble component (% by weight)=[weight of deionized water (g)×solid contents of filtrate (% by weight)]/ 0.500 (g)  (2)

(c) Ropiness of gel

The swelled gel of the sample which had undergone the determination of absorption ratio in (a) above was examined by the touch of a finger to rate the ropiness thereof.

(d) Stability of gel to withstand effects of aging

Accurately two (2.0) g of a given absorbent resin powder was impregnated with 50 g of human urine taken from 10 male adults and left standing at 37° C. The swelled gel of the sample powder was visually examined for the degree of deterioration after varying intervals of 6 hours, 12 hours, and 18 hours. The degree of deterioration was rated on a three-point scale o–Δ–X, wherein o stands for retention of the shape of swelled gel, Δ for partial break down of the shape of the swelled gel, and X for the collapse of the shape of the swelled gel accompanied by conversion into a slurry.

EXAMPLE 1

In a jacketed twin arm type kneader of stainless steel having an inner volume of 10 liters and provided with two sigma (Σ) type vanes, 5,500 g of an aqueous solution of an aerylate type monomer consisting of 75 mol % of sodium acrylate and 25 mol % of acrylic acid (monomer concentration 30% by weight) and 8.09 g of polyethylene glycol diacrylate (average ethylene oxide unit number 7) (0.1 mol % based on the amount of the monomer) as a cross-linking agent (I) were placed. The air entrapped in the reaction system was displaced by blowing nitrogen gas into the kneader.

The monomer in the reaction system was polymerized by heating the reactants in the kneader by passing hot water at 35° C. through the jacket, adding 2.5 g of ammonium persulfate and 2.5 g of sodium hydrogen sulfite as polymerization initiators to the reactants, and agitating the contents of the kneader by rotating the sigma vanes at 65 r.p.m. The polymerization was continued for 1 hour. After the reaction was completed, 2,000 g of finely divided hydrated gel particles were placed on a metallic net of a mesh size of 0.3 mm and dried thereon with hot air at a temperature of 180° C. for 2 hours. The dried particles were pulverized by the use of a hammer mill to obtain an absorbent resin. This absorbent resin was found to have an absorption ratio of 58.9 g/g and a water-soluble component content of 8.3% (see Table 1).

Control 1

An absorbent resin was obtained by following the procedure of Example 1, except that the hydrated gel was dried with hot air at a temperature of 150° C. for 2 hours. This absorbent resin was found to have an absorption ratio of 48.7 g/g and a water-soluble component content of 8.2% (see Table 1).

Control 2

An absorbent resin was obtained by following the procedure of Example 1, except that 9.92 g (0.1 mol % based on the amount of the monomer) of polypropylene glycol diacrylate (propylene oxide average unit number 7) was used in the place of the cross-linking agent (I). This absorbent resin was found to have an absorption ratio of 48.3 g/g and a water-soluble component content of 11.1% (see Table 1).

Control 3

An absorbent resin was obtained by following the procedure of Control 2, except that the hydrated gel was dried with hot air at a temperature of 150° C. for 2 hours. This absorbent resin was found to have an absorption ratio of 46.0 g/g and a water-soluble component content of 10.2% (see Table 1).

EXAMPLE 2

An absorbent resin was obtained by following the procedure of Example 1, except that 7.52 g of (0.07 mol %) of a cross-linking agent represented by the following formula VII

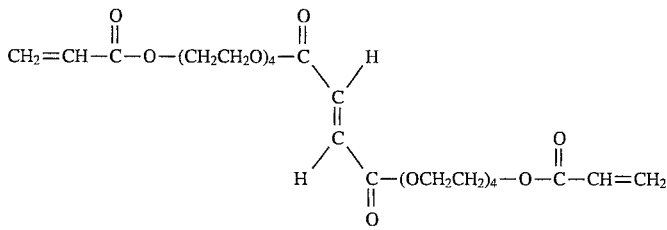

(VII)

was used in the place of the cross-linking agent (I). This absorbent resin was found to have an absorption ratio of 62.2 g/g and a water-soluble component of 8.3% (see Table 1).

Control 4

An absorbent resin was obtained by following the procedure of Example 2, excepting that the hydrated gel was dried with hot air at a temperature of 150° C. for 2 hours. This absorbent resin was found to have an absorption ratio of 52.7 g/g and a water-soluble component content of 8.1% (see Table 1).

It is noted from Examples 1 to 2 and Controls 1 to 4 that the absorption ratios were lower when the temperature of heat treatment was 150° C. and when cross-linking agents other than cross-linking agent (I) of this invention were used.

EXAMPLE 3

An absorbent resin was obtained by following the procedure of Example 1, except that 9.66 g (0.07 mol %) of a cross-linking agent represented by the following formula VIII was used in the place of the cross-linking agent (I). This absorbent resin was found to have an absorption ratio of 56.4% and a water-soluble component content of 10.3% (see Table 2).

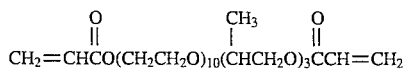

(VIII)

Control 5

An absorbent resin was obtained by following the procedure of Example 3, except that the amount of the cross-linking agent (I) to be used was changed to 4.14 g (0.03 mol % based on the amount of the monomer) and the hydrated gel was dried with hot air at a temperature of 150° C. for 2 hours. This absorbent resin was found to have an absorption ratio of 55.2 g/g and a water-soluble component content of 18.4%. The gel of the resin was markedly ropy and deficient in stability to offer continued resistance to the adverse action of urine (see Table 2).

Control 6

An absorbent resin was obtained by following the procedure of Example 3, except that 1.66 g (0.03 mol % based on the amount of the monomer) of trimethylol propane triacrylate was used in the place of the cross-linking agent (I). This absorbent resin was found to have an absorption ratio of 56.2 g/g and a water-soluble component content of 20.2%. The gel was ropy and deficient in its ability to withstand the effect of aging (see Table 2). It is noted from Example 3 and Controls 5 to 6 that the water-soluble component contents were large, the ropiness of the gel was conspicuous, and the ability of the gel to withstand the effect of aging was inferior when absorbent resins having substantially the same levels of absorption ratio were produced by methods other than the method conforming to this invention.

EXAMPLE 4

In the same twin arm type kneader as used in Example 1, 5,500 g of an aqueous solution of a monomer component consisting of 75 mol % of potassium acrylate and 20 mol % of acrylic acid and 5 mol % of acrylamide (monomer concentration 35% by weight) was placed and 14.1 g (0.1 mol % based on the amount of the monomer) of the compound represented by the following formula IX was added as a cross-linking agent (I) to the aqueous solution and the air entrapped in the reaction system was displaced by blowing nitrogen gas into the kneader.

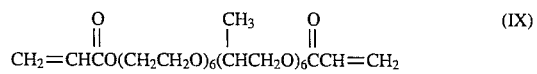

(IX)

Then, the monomer in the reactants was polymerized by adding 2.0 g of sodium persulfate and 0.1 g of L-ascorbic acid as a polymerization initiator to the reactants and agitating the contents of the kneader by rotating the sigma vanes at 65 r.p.m.

After the reaction was completed, finely divided gel particles were placed on a metallic net having a mesh size of 0.3 mm and dried with hot air at a temperature of 200° C. for 1 hour. The dried particles were pulverized by the use of a hammer mill to obtain an absorbent resin. This absorbent resin was found to have an absorption ratio of 59.2 g/g and a water-soluble component content of 12.4% (see Table 3).

EXAMPLE 5

An absorbent resin was obtained by following the procedure of Example 4, except that 60.5 g (0.15 mol % based on the amount of the monomer) of polyethylene glycol diacrylate (ethylene oxide average unit number 45) was used in the place of cross-linking agent (I). This absorbent resin was found to have an absorption ratio of 57.3 g/g and a water-soluble component content of 12.1% (see Table 3).

Control 7

An absorbent resin was obtained by following the procedure of Example 4, except that 0.72 g (0.03 mol % based on the amount of the monomer) of methylene bis-acrylamide was used in the place of cross-linking agent (I). This absorbent resin was found to have an absorption ratio of 55.9 g/g and a water-soluble component content of 20.4%. The gel was ropy and deficient in its ability to offer continued resistance to the action of urine (see Table 3).

Control 8

An absorbent resin was obtained by following the procedure of Example 4, except that the finely divided gel particles were dried with hot air at a temperature of 120° C. for 4 hours. This absorbent resin was found to have an absorption ratio of 46.2 g/g and a water-soluble component content of 11.8%. The absorption ratio is lower than that of Example 4 (see Table 3).

EXAMPLE 6

An absorbent resin was obtained by mixing 100 parts by weight of the absorbent resin obtained in Example 1 with a hydric solution containing of 0.3 parts of glycerol, 2 parts of water, and 8 parts of isopropanol as a solution of the cross-linking agent (III), placing the resultant mixture in a drying device kept at 180° C., and heating the reactants therein for 20 minutes to effect the cross-linking reaction. This absorbent resin had an absorption ratio of 58 g/g and the gel of the resin exhibited satisfactory stability to withstand the effects of aging (see Table 4).

Control 9

An absorbent resin was obtained by following the procedure of Example 6, except that the absorbent resin obtained in Control 6 was used instead. This absorbent resin had an absorption ratio of 55 g/g. The stability of the gel to withstand the effects of aging was slightly better than that of the gel of Control 6 but was still short of being satisfactory. The gel was ropy (see Table 4).

Control 10

An absorbent resin was obtained by following the procedure of Example 6, except that the absorbent resin obtained in Control 6 was mixed with the solution of cross-linking agent (II) and the resultant mixture was heated for 40 minutes. The absorption ratio of the absorbent resin was 47 g/g. The gel of the resin showed highly satisfactory stability to withstand the effects of aging. It was ropy (see Table 4).

TABLE 1

|  | Heat-treatment temperature (°C.) | Absorption ratio (g/g) | Content of water-soluble component (%) | Ropiness of gel | Gel stability to withstand effect of aging (6 hrs/12 hrs/18 hrs) |
| --- | --- | --- | --- | --- | --- |
| Example 1 | 180 | 59 | 8 | no | ○/○/△ |
| Control 1 | 150 | 49 | 8 | no | ○/○/△ |
| Control 2 | 180 | 48 | 11 | no | ○/○/△ |
| Control 3 | 150 | 46 | 10 | no | ○/○/△ |
| Example 2 | 180 | 62 | 8 | no | ○/○/△ |
| Control 4 | 150 | 53 | 8 | no | ○/○/△ |

TABLE 2

|  | Heat-treatment temperature (°C.) | Absorption ratio (g/g) | Content of water-soluble component (%) | Ropiness of gel | Gel stability to withstand effect of aging (6 hrs/12 hrs/18 hrs) |
| --- | --- | --- | --- | --- | --- |
| Example 3 | 180 | 56 | 10 | no | ○/○/△ |
| Control 5 | 150 | 55 | 18 | yes | ○/△/X |
| Control 6 | 180 | 56 | 20 | yes | X/X/X |

TABLE 3

|  | Heat-treatment temperature (°C.) | Absorption ratio (g/g) | Content of water-soluble component (%) | Ropiness of gel | Gel stability to withstand effect of aging (6 hrs/12 hrs/18 hrs) |
| --- | --- | --- | --- | --- | --- |
| Example 4 | 200 | 59 | 12 | no | ○/○/△ |
| Example 5 | 200 | 57 | 12 | no | ○/○/△ |
| Control 7 | 120 | 56 | 20 | yes | △/X/X |
| Control 8 | 120 | 46 | 12 | no | ○/○/△ |

TABLE 4

|  | Absorption ratio (g/g) | Content of water-soluble component (%) | Ropiness of gel | Gel stability to withstand effect of aging (6 hrs/12 hrs/18 hrs) |
| --- | --- | --- | --- | --- |
| Example 6 | 58 | 8 | no | ○/○/○ |
| Control 9 | 55 | 21 | yes | ○/△/X |
| Control 10 | 47 | 20 | yes | ○/○/△ |

What is claimed is:

1. A method for producing an absorbent resin comprising polymerizing a water-soluble monoethylenically unsaturated monomer in the presence of a cross-linking agent, said cross-linking agent possessing at least two polymerizable unsaturated groups and between said two polymerizable unsaturated groups at least one unit represented by the formula V:

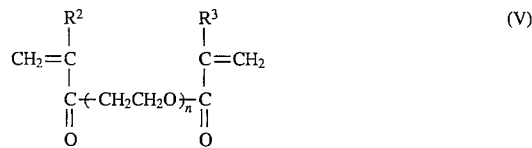

wherein $R^2$ and $R^3$ are independently a hydrogen atom or a methyl group and n is a number in the range of from 2 to 100, said cross-linking agent is used in a proportion in the range of from 0.01 to 0.3 mol % based on the amount of said water-soluble monoethylenically unsaturated monomer, and heat-treating the resultant polymer at a temperature in the range of from 160° to 230° C. in the presence of another cross-linking agent having at least two reacting groups capable of reacting with functional groups of said polymer.

2. A method according to claim 1, wherein said cross-linking agent of formula (V) is used in a proportion in the range of from 0.03 to 0.2 mol % based on the amount of said water-soluble monoethylenically unsaturated monomer.

3. A method according to claim 1, wherein said water-soluble monoethylenically unsaturated monomer contains 50% by weight or more of at least one member selected from the group consisting of acrylic acid and alkali metal salts and amine salts.

4. A method according to claim 1, wherein said heat treatment of said polymer is carried out at a temperature in the range of from 180° to 200° C.

5. A method according to claim 1, wherein said another cross-linking agent is a polyalcohol.

6. A method according to claim 1, wherein the amount of said another cross-linking agent is in the range of 0.005 to 5% by weight based on the amount of said polymer.

* * * * *